United States Patent
Shibata et al.

(10) Patent No.: US 12,014,578 B2
(45) Date of Patent: *Jun. 18, 2024

(54) AUTHENTICATION DEVICE, AUTHENTICATION METHOD, AND RECORDING MEDIUM

(71) Applicant: NEC Corporation, Tokyo (JP)

(72) Inventors: Takashi Shibata, Tokyo (JP); Shoji Yachida, Tokyo (JP); Chisato Funayama, Tokyo (JP); Masato Tsukada, Tokyo (JP); Yuka Ogino, Tokyo (JP); Keiichi Chono, Tokyo (JP); Emi Kitagawa, Tokyo (JP); Yasuhiko Yoshida, Tokyo (JP); Yusuke Mori, Tokyo (JP)

(73) Assignee: NEC CORPORATION, Tokyo (JP)

( * ) Notice: Subject to any disclaimer, the term of this patent is extended or adjusted under 35 U.S.C. 154(b) by 8 days.

This patent is subject to a terminal disclaimer.

(21) Appl. No.: 17/681,995

(22) Filed: Feb. 28, 2022

(65) Prior Publication Data

US 2022/0189212 A1 Jun. 16, 2022

Related U.S. Application Data

(63) Continuation of application No. 17/279,237, filed as application No. PCT/JP2018/036424 on Sep. 28, 2018.

(51) Int. Cl.
*G06V 40/70* (2022.01)
*G06V 20/52* (2022.01)
(Continued)

(52) U.S. Cl.
CPC .............. *G06V 40/70* (2022.01); *G06V 20/52* (2022.01); *G06V 40/103* (2022.01);
(Continued)

(58) Field of Classification Search
CPC ...... G06V 40/70; G06V 20/52; G06V 40/103; G06V 40/171; G06V 40/19; G06V 40/197;
(Continued)

(56) References Cited

U.S. PATENT DOCUMENTS

2006/0165264 A1* 7/2006 Saitoh .................. G06V 40/103
382/115
2007/0291998 A1 12/2007 Takizawa et al.
(Continued)

FOREIGN PATENT DOCUMENTS

JP H09-198531 A 7/1997
JP 2000-102524 A 4/2000
(Continued)

OTHER PUBLICATIONS

Labati et al. Biometric Recognition in Automated Border Control: A Survey—2016 (Year: 2016).*
(Continued)

*Primary Examiner* — Nizar N Sivji

(57) ABSTRACT

The disclosure is detecting an authentication target who is moving in a predetermined direction in a video; inputting a first image in which an entire body of the target; calculating characteristic information from an image of the entire body in the first image, comparing the calculated characteristic information with characteristic information of the entire body stored in first memory that stores characteristic information of entire bodies of targets, and extracting candidate information of the targets from the first memory based on a first authentication result; inputting a second image in which an iris of the target; and comparing characteristic information of irises stored in second memory that stores the characteristic information of the irises of targets with characteristic information of an iris from the second image, calculating a verification score, executing second authenti-
(Continued)

cation on the target in the second image based on the verification score, and outputting an authentication result.

9 Claims, 10 Drawing Sheets

(51) Int. Cl.
*G06V 40/10* (2022.01)
*G06V 40/16* (2022.01)
*G06V 40/18* (2022.01)
*G06V 40/19* (2022.01)

(52) U.S. Cl.
CPC ............ *G06V 40/171* (2022.01); *G06V 40/19* (2022.01); *G06V 40/197* (2022.01); *G06V 2201/07* (2022.01)

(58) Field of Classification Search
CPC .. G06V 2201/07; G06V 40/172; G06V 40/23; A61B 5/0077; A61B 5/107; A61B 5/1113; A61B 5/112; A61B 5/1171
See application file for complete search history.

(56) References Cited

U.S. PATENT DOCUMENTS

| | | |
|---|---|---|
| 2018/0204058 A1 | 7/2018 | Yoo et al. |
| 2021/0279475 A1* | 9/2021 | Tusch ................. H04L 63/0861 |
| 2021/0350126 A1* | 11/2021 | Shibata ................. G06V 40/103 |
| 2022/0044014 A1* | 2/2022 | Shibata ................. G06V 40/161 |
| 2022/0180662 A1* | 6/2022 | Shibata ................. G06V 40/197 |
| 2022/0189207 A1* | 6/2022 | Shibata ................. G06V 40/197 |
| 2022/0254193 A1* | 8/2022 | Shibata ................. G06V 40/197 |
| 2022/0392262 A1* | 12/2022 | Shibata ................. G06V 40/19 |

FOREIGN PATENT DOCUMENTS

| | | | |
|---|---|---|---|
| JP | 2000-148985 A | | 5/2000 |
| JP | 2003-058888 A | | 2/2003 |
| JP | 2004-171241 A | | 6/2004 |
| JP | 2004171241 A | * | 6/2004 |
| JP | 2005-227933 A | | 8/2005 |
| JP | 2005227933 A | * | 8/2005 |
| JP | 2005-242677 A | | 9/2005 |
| JP | 2007-334623 A | | 12/2007 |
| JP | 2009-015518 A | | 1/2009 |
| JP | 2011-150497 A | | 8/2011 |
| JP | 2011150497 A | * | 8/2011 |
| WO | 2014/172480 A2 | | 10/2014 |

OTHER PUBLICATIONS

Multimodal Person Authentication System Using Features of Utterance—2012 (Year: 2012).*
Unimodal and Multimodal Biometric Sensing Systems: A Review—2016 (Year: 2016).*
U.S. Notice of Allowance dated Apr. 27, 2023 in U.S. Appl. No. 17/682,000.
International Search Report for PCT Application No. PCT/JP2018/036424, dated Dec. 18, 2018.
English translation of Written opinion for PCT Application No. PCT/JP2018/036424, dated Dec. 18, 2018.
Supplementary Partial European Search Report for EP Application No. 18934956.6 dated Aug. 20, 2021.
Ruggero Donida Labati et al., "Biometric Recognition in Automated Border Control", ACM Computing Surveys, vol. 49, No. 2, Article 24, pp. 1-39, Jun. 30, 2016 (Jun. 30, 2016), XP058484556, USA.
Extended European Search Report for EP Application No. 18934956.6 dated Dec. 17, 2021.

* cited by examiner

Fig.7

| | | ID | 1 | 2 | 3 | ... |
|---|---|---|---|---|---|---|
| RIGHT | | CHARACTERISTIC INFORMATION | | | | ... |
| | | RELIABILITY SCORE | 80% | 40% | 10% | ... |
| LEFT | | CHARACTERISTIC INFORMATION | | | | ... |
| | | RELIABILITY SCORE | 20% | 60% | 90% | ... |

17a

AUTHENTICATION DEVICE, AUTHENTICATION METHOD, AND RECORDING MEDIUM

The present application is a Continuation application of Ser. No. 17/279,237 filed on Mar. 24, 2021, which is a National Stage Entry of PCT/JP2018/036424 filed on Sep. 28, 2018, the contents of all of which are incorporated herein by reference, in their entirety.

TECHNICAL FIELD

The example embodiments relates to an authentication device or the like that authenticates a target.

BACKGROUND ART

Personal authentication based on an individual difference of a living body (Biometrics-based authentication) has a lower risk of leakage and theft than a password or the like created by a user. For this reason, there are increasing examples of introducing the personal authentication based on the individual difference of the living body to identify the individual and confirm the right or for security protection. A personal authentication technique based on the individual difference of the living body has been known that uses fingerprints (Fingerprint), veins (Vein), faces (Face), irises (Iris), voices (Voice), or the like as biometric information.

Among these, in face authentication and iris authentication, positions (face and eyes) of authentication targets are almost the same, and multi-modal authentication in which the face authentication and the iris authentication are combined has been developed (refer to cited documents 1 and 2).

CITATION LIST

Patent Literature

[PTL 1] JP 2000-102524 A
[PTL 2] JP 2005-242677 A

SUMMARY

Technical Problem

There is a need for companies and organizations that operate commercial facilities and large event venues to utilize walkthrough authentication for an entrance and exit management system in order to enhance security measures and enhance convenience of the user side in entrance and exit management of a large number of users. In the walkthrough authentication, a living body (user) to be authenticated only walks through a predetermined section without stopping in front of an authentication camera. As a result, authentication processing can be executed at high speed even if the number of users to be authenticated is large and without making the user side conscious of the authentication processing. When the face authentication and the iris authentication are applied to the walkthrough authentication in combination as the multi-modal authentication, it is preferable because authentication data can be collected only by performing imaging using a camera without having contact with the users.

However, because the user moves in the walkthrough authentication, a time period spent on the authentication is limited. Specifically, a time period from a time when the user enters an authentication gate entrance and images an image to be used for authentication (authentication start time) to a time when the user ends the authentication and passes through an authentication gate exit (authentication completion time) is limited to about several seconds. Therefore, if the positions of the authentication regions are close to each other as in the combination of the face authentication and the iris authentication, it is necessary to execute two types of authentication processing at high speed at almost the same timings, and a plurality of cameras and a large number of hardware resources are required.

The disclosure has been made in view of the above problems, and one of objects of the disclosure is to provide an authentication device or the like that can execute authentication with high accuracy on an authentication target who is moving with less hardware resources and within a predetermined time period.

Solution to Problem

In view of the above problems, an authentication device which is a first aspect of the disclosure includes:

detection means for detecting an authentication target who is moving in a predetermined direction in a video of a predetermined area;

first image input means for inputting a first image in which an entire body of the detected target is imaged;

first storage means for storing characteristic information of entire bodies of one or more targets to be authenticated;

first authentication means for calculating characteristic information from the image of the entire body of the target imaged in the first image, comparing the calculated characteristic information with the characteristic information of the entire body stored in the first storage means, and extracting candidate information of the one or more targets from the first storage means based on a comparison result;

second image input means for inputting a second image in which an iris of at least one of a right eye and a left eye of the target who is detected by the detection means and is moving in the predetermined direction is imaged;

second storage means for storing characteristic information of irises of the right eyes and the left eyes of the one or more targets to be authenticated; and second authentication means for calculating a verification score by comparing the characteristic information of the iris calculated from the second image with the characteristic information of the one or more irises stored in the second storage means for each target included in the candidate information, authenticating the target imaged in the second image based on the calculated verification score, and outputting an authentication result.

An authentication method that is a second aspect of the disclosure includes:

detecting an authentication target who is moving in a predetermined direction in a video of a predetermined area;

inputting a first image in which an entire body of the detected target is imaged;

calculating characteristic information from the image of the entire body of the target imaged in the first image, comparing the calculated characteristic information with characteristic information of the entire body stored in first storage means that stores characteristic information of entire bodies of one or more targets to be authenticated to execute first authentication, and extracting candidate information of the one or more targets from the first storage means based on a result of the first authentication;

inputting a second image in which an iris of at least one of a right eye and a left eye of the target who is detected and is moving in the predetermined direction is imaged; and comparing characteristic information of one or more irises stored in second storage means that stores characteristic information of the irises of the right eyes and the left eyes of the one or more targets to be authenticated with characteristic information of the iris calculated from the second image for each target included in the candidate information to calculate a verification score, executing second authentication on the target imaged in the second image based on the calculated verification score, and outputting an authentication result.

An authentication program that is a third aspect of the disclosure and causes a computer to achieve processing including:

detecting an authentication target who is moving in a predetermined direction in a video of a predetermined area;

inputting a first image in which an entire body of the detected target is imaged;

calculating characteristic information from the image of the entire body of the target imaged in the first image, comparing the calculated characteristic information with characteristic information of the entire body stored in first storage means that stores characteristic information of entire bodies of one or more targets to be authenticated to execute first authentication, and extracting candidate information of the one or more targets from the first storage means based on a result of the first authentication;

inputting a second image in which an iris of at least one of a right eye and a left eye of the target who is detected and is moving in the predetermined direction is imaged; and comparing characteristic information of one or more irises stored in second storage means that stores characteristic information of the irises of the right eyes and the left eyes of the one or more targets to be authenticated with characteristic information of the iris calculated from the second image for each target included in the candidate information to calculate a verification score, executing second authentication on the target imaged in the second image based on the calculated verification score, and outputting an authentication result.

The authentication program may be stored in a storage medium.

BRIEF DESCRIPTION OF DRAWINGS

FIG. 7 is a diagram illustrating an exemplary configuration of data stored in a second storage unit.

EXAMPLE EMBODIMENT

Figure 1:
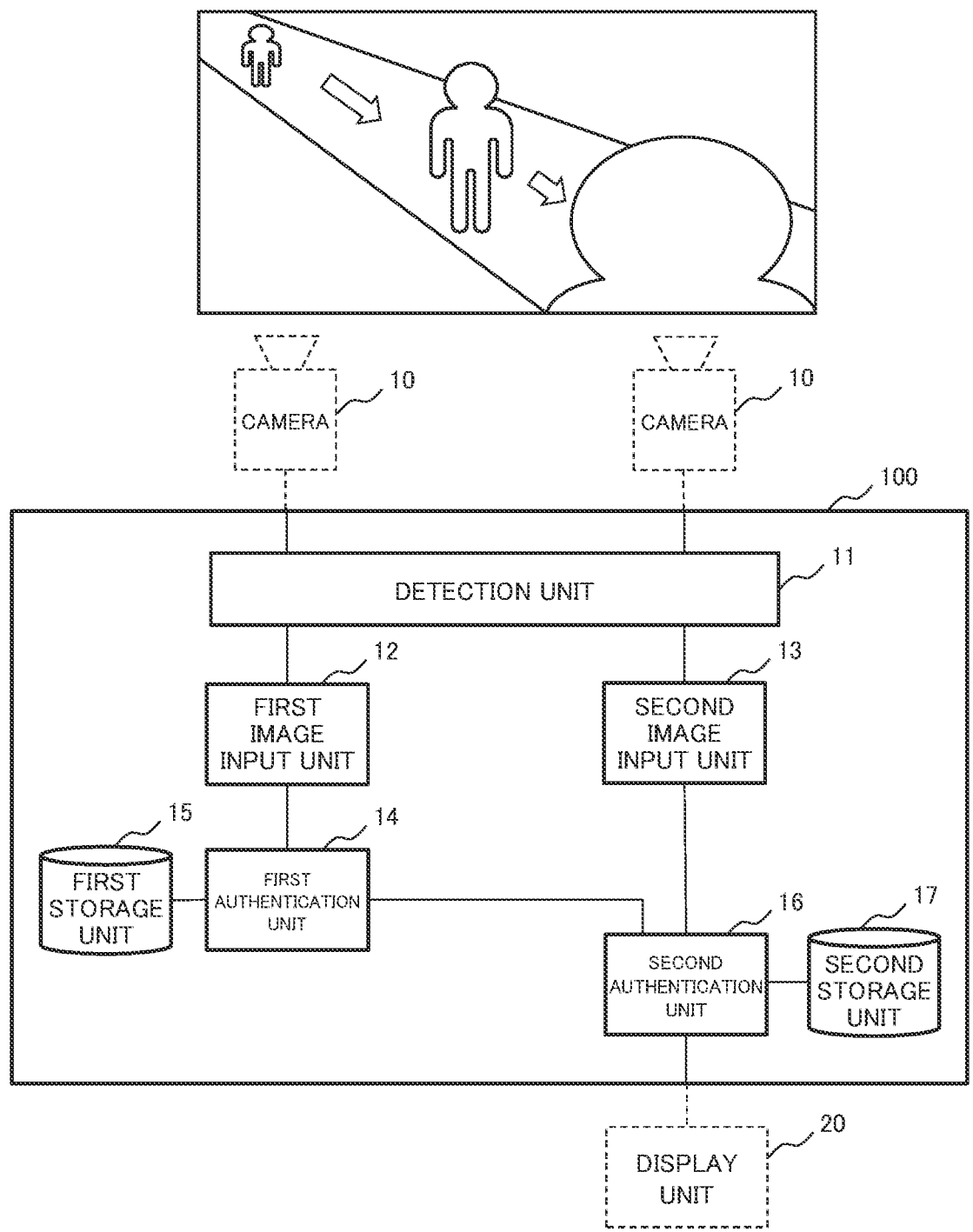
FIG. 1 is a diagram of a configuration of a biometric authentication device according to a first example embodiment of the disclosure.

Hereinafter, each example embodiment will be described in detail with reference to the drawings. In the following description of the drawings, the same or similar part are denoted with the same or similar reference numerals. However, the drawings schematically illustrate the configurations according to the example embodiments. Moreover, the example embodiments described below are merely examples, and can be appropriately modified to the extent that they are essentially the same.

Authentication in each example embodiment is mainly biometric authentication. An authentication target is mainly a living body including humans (user), animals, or the like. The authentication target may include, for example, a mannequin, other than a living body. When iris authentication is performed, right and left eyes of the target (including artificial eyes for impersonation) are authenticated. In the description of each example embodiment below, the target of the authentication is also referred to as a "target user".

Information used for biometric authentication includes a plurality of types of information such as an ultrasound graph, an image of a living body, or audio data. In the following description, for example, an image (specifically, iris image) will be mainly described. However, this does not intend to limit each example embodiment.

First Example Embodiment

To execute multi-modal authentication in a non-contact manner with a user who is an authentication target, it is preferable to use gait authentication, human shape authentication, face authentication, iris authentication, or the like. The human shape authentication indicates authentication executed on the basis of features of the body of the authentication target (for example, height, width of body, limb length, contour of face, or the like, or combination of these). The gait authentication indicates authentication executed on the basis of features of a walking pattern of the authentication target (for example, posture at the time of walking, stride length, arm swing, habitual movement left-right asymmetry (whether to hole shoulder bag on the same side or the like), or the like or combination of these). Among these, with the gait authentication and the human shape authentication, it is easy to execute authentication from an image of an entire body of an authentication target user who can be imaged from a distance. With the iris authentication, an authentication result with the highest accuracy can be expected if left and right eyes can be accurately imaged near the authentication target user. In a case of walkthrough authentication, the target user moves from an entrance to an exit of an authentication gate in several seconds to several tens of seconds, although the time period depends on individuals. Therefore, the gait authentication or the human shape authentication using the entire body image is executed on the target user near the entrance of the remote authentication gate as first authentication, and in addition, iris authentication using images of the left and right eyes is executed on the target user who has moved to the vicinity of the exit of the authentication gate on the basis of a result of the first authentication. Because candidates of the target user are narrowed by the first authentication, the number of target user candidates on which the iris authentication is executed is considerably small. As a result, an authentication result with high accuracy can be quickly obtained. Hereinafter, a biometric authentication device for executing the walk-through authentication as described above will be described in detail.

Biometric Authentication Device

As illustrated in FIG. 1, a biometric authentication device 100 includes a detection unit 11, a first image input unit 12, a second image input unit 13, a first authentication unit 14, a first storage unit 15, a second authentication unit 16, and a second storage unit 17.

The detection unit 11 detects a target user to be authenticated who is moving in a predetermined direction in a video of a predetermined area from an entrance gate to an exit gate in an authentication execution area.

Figure 2:
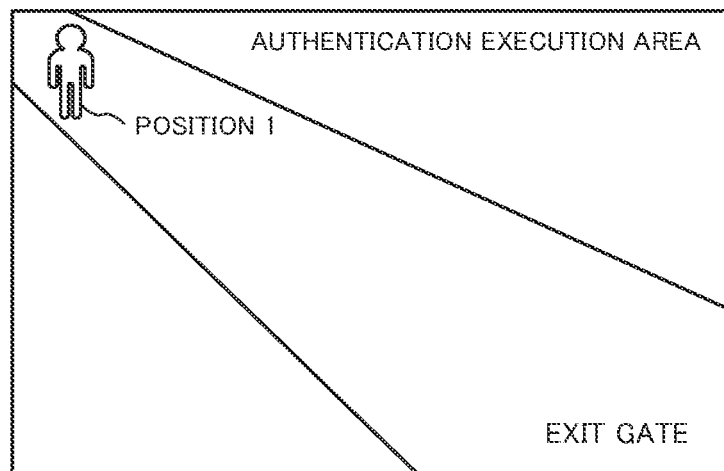
FIG. 2 is a diagram of an image of a target user who moves in a specific direction.

The detection unit 11 is connected to an external camera 10 as illustrated in FIG. 1. The camera 10 is a camera that images a user to be authenticated. There may be one or a plurality of cameras 10. The detection unit 11 detects a user who moves in a specific direction in an image imaged by the camera 10 (including moving image, still image. The same applies below). The movement in the specific direction means that a user walks from the entrance gate to the exit gate of the authentication execution area, for example, in a case of the walkthrough authentication. The specific direction means a direction from the entrance gate to the exit gate. In a case of the authentication execution area illustrated in FIG. 2, the camera 10 first images the user at a position 1 near the entrance gate. In the authentication execution area in FIG. 2, the entrance gate is arranged on the inner side, and the exit gate is arranged on the front side. The camera 10 is fixed at a position (wall, gate, or the like) where an image as illustrated in FIG. 2 can be captured.

When there is a user who moves from the position 1 to a position 2 advanced by a predetermined distance in the specific direction (refer to FIG. 3) in the image of the user imaged by the camera 10, the detection unit 11 determines that the above user is a target user to be authenticated, and detects the user as the target user. Image data of a region including an entire body of the detected target user is input to the first image input unit 12 as a first image (refer to FIG. 3). Moreover, when there is a user who moves from the position 2 to a position 3 advanced by a predetermined distance in the specific direction (refer to FIG. 4) in the image of the user imaged by the camera 10, the detection unit 11 determines that the above user is a target user to be authenticated again, and detects the user as the target user. Image data of a region including left and right eyes of the detected target user is input to the second image input unit 13 as a second image (refer to FIG. 4).

Processing for selecting image regions including the body of the user (region including entire body of target user and region including left and right eyes) may be transferred to the first image input unit 12 or the second image input unit 13 after being executed by the detection unit 11 or may be executed by the first image input unit 12 or the second image input unit 13 that has received the image captured by the camera 10. Note that the above processing may be executed by the camera 10.

When detecting the movement of the target user in a direction other than the predetermined direction, the detection unit 11 may stop an output of an image to the first image input unit 12 and the second image input unit 13. That is, the first image input unit 12 and the second image input unit 13 stop an input of the image of the target user who starts to move in the direction other than the predetermined direction. This is because, even if the user is wrongly determined as a target user once, there is a case where authentication is stopped in the middle because the user is an observer or a maintenance person in the authentication execution area or because the target user has left something, or the like.

The first image input unit 12 receives the input of the first image (refer to FIG. 3) obtained by imaging the region including the entire body of the user who moves in the specific direction from the detection unit 11.

The first storage unit 15 stores characteristic information regarding entire bodies of one or more users to be authenticated. Here, the characteristic information regarding the entire body is characteristic information regarding a human shape used for human shape authentication, characteristic information regarding a gait used for gait authentication, or the like. The characteristic information regarding the human shape is, for example, a pattern such as a height, a width of a body, or the like extracted from a silhouette of an entire body image. The silhouette of the entire body image is extracted, for example, using a background difference between an image of a color camera and an image of an infrared camera. The characteristic information regarding the gait is, for example, Spatio-Temporal Histograms of Oriented Gradient (STHOG) characteristic information that is a gait feature based on a time-space luminance gradient, frequency region characteristic information using a Gait Silhouette Volume, or the like. As described above, in the first authentication, it is difficult to know a degree of light at a distance, and in addition, it is difficult to control light. Therefore, it is desirable to surely and easily extract the characteristic information by using the silhouette of the target user.

The first authentication unit 14 calculates the characteristic information from the image of the entire body of the target user imaged in the first image, compares the calculated characteristic information with characteristic information of the entire body stored in the first storage unit 15, and extracts candidate information of one or more target users from the first storage unit 15 on the basis of a comparison result. The candidate information is information that can specify a candidate of the target user and is, for example, an IDentifier (ID) of the target user. The first authentication has a function as a prefilter of second authentication.

The first authentication unit 14 outputs the extracted candidate information of the target user to the second authentication unit 16.

The second image input unit 13 inputs the second image (refer to FIG. 4) obtained by imaging an iris of at least one of the right eye and the left eye of the target user who is moving in the predetermined direction and is detected by the detection unit 11. Which one of the left eye and the right eye the imaged eye is can be determined according to a shape of an inner corner of each eye or the like. It is preferable that the second image input unit 13 input images of both eyes. However, in a case where the camera 10 cannot acquire the image of one eye (for example, it is not possible to perform imaging because bangs cover eye, it is not possible to perform imaging due to reflection of glasses, or the like), an image of another eye that can be imaged is imaged.

The second storage unit 17 stores characteristic information of irises of the right and the left eyes of one or more users to be authenticated. Note that the characteristic information of the iris is, for example, an iris code (refer to characteristic information in FIG. 7) generated on the basis of the Daugman algorithm.

The second authentication unit 16 receives the input of the candidate information from the first authentication unit 14. The second authentication unit 16 compares the characteristic information of the iris calculated from the second image and the characteristic information of one or more irises stored in the second storage unit 17 and calculates a verification score for each target user included in the candidate information, authenticates the target user imaged in the first image and the second image on the basis of the calculated verification score, and outputs an authentication result. The verification score is a value of a result obtained by calculating the number of bits different between an iris code of the target user and an iris code registered in the second storage unit 17 (calculate hamming distance).

The second authentication unit 16 calculates the characteristic information of the iris from the second image associated with left/right information for each target user included in the candidate information. The second image associated with the left/right information indicates an iris image of the right eye tagged as "right eye" and an iris image of the left eye tagged as "left eye" (refer to second image in FIG. 4). Note that either one of the left and the right eyes may be a tagged iris code. A case where the iris code is used as the characteristic information of the iris will be described as an example. The second authentication unit 16 specifies a boundary line of an iris from an image of an iris received from the second image input unit 13 and extracts an iris portion. Moreover, the second authentication unit 16 encodes an iris pattern by applying a two-dimensional Gabor filter to information regarding the extracted iris portion and generates an iris code. The iris code is, for example, a 2048-bit digital encoding code.

The second authentication unit 16 compares the calculated characteristic information with characteristic information of a plurality of users associated with the left/right information stored in the second storage unit 17. Specifically, the second authentication unit 16 compares the characteristic information with characteristic information of only the right eye stored in the second storage unit 17 in a case of an iris image tagged with the right eye, and compares the characteristic information with characteristic information of only the left eye stored in the second storage unit 17 in a case of an iris image tagged with the left eye. The second authentication unit 16 obtains a verification score as a result of comparison. For example, when the calculated verification score is equal to or more than a predetermined threshold, the second authentication unit 16 authenticates that the user imaged in the second image is a registered user (valid user), and when the verification score is less than the predetermined threshold, the second authentication unit 16 authenticates that the user imaged in the second image is not the registered user. The second authentication unit 16 outputs an authentication result to an external display unit 20. The display unit 20 is a liquid crystal display or the like, and can display the authentication result to be browsable by the target user or an administrator of the authentication execution area. Note that the user imaged in the second image is the user imaged in the first image. In addition, the authentication result may be notified with voice notifications by a speaker or a buzzer, lighting of lamps, or the like.

Operation of Biometric Authentication Device

An operation of the biometric authentication device 100 according to the first example embodiment will be described with reference to the flowchart in FIG. 5. Note that it is assumed that the first storage unit 15 store in advance the characteristic information of the entire body of the plurality of users who may be an authentication target. It is assumed that the second storage unit 17 store in advance characteristic information of irises of the right eyes and the left eyes of the plurality of users who may be an authentication target.

In step S101, the detection unit 11 detects a user in a video of the authentication execution area imaged by the camera 10 (refer to FIG. 2).

Figure 3:
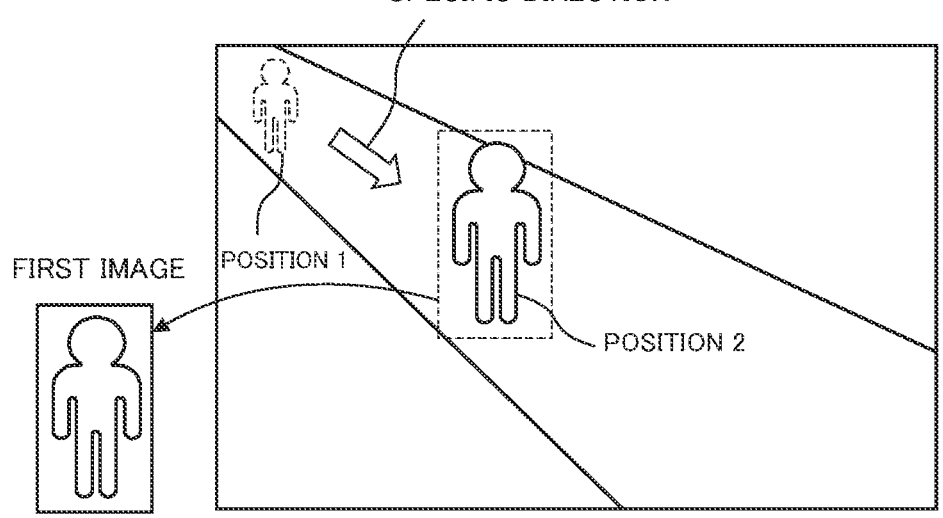
FIG. 3 is a diagram of a first image acquired from the image of the target user who moves in the specific direction.

In step S102, the detection unit 11 detects whether the user is moving in the direction from the entrance to the exit of the authentication gate (refer to FIG. 3). As a result of the detection, if the user is moving in the direction from the entrance to the exit, the detection unit 11 sets this user as an authentication target user, acquires an image of an entire body of the target user from the camera 10, and outputs the image to the first image input unit 12. As a result of the detection, if the user is not moving in the direction from the entrance to the exit, the procedure returns to step S101.

In step S103, the first image obtained by imaging the entire body of the target user is input to the first image input unit 12.

In step S104, the first authentication unit 14 calculates the characteristic information from the image of the entire body of the target user imaged in the first image, compares the calculated characteristic information with the characteristic information of the entire body stored in the first storage unit 15, and extracts candidate information of one or more target users from the first storage unit 15 on the basis of a comparison result.

In step S105, the first authentication unit 14 temporarily holds the extracted candidate information of the target user.

Figure 4:
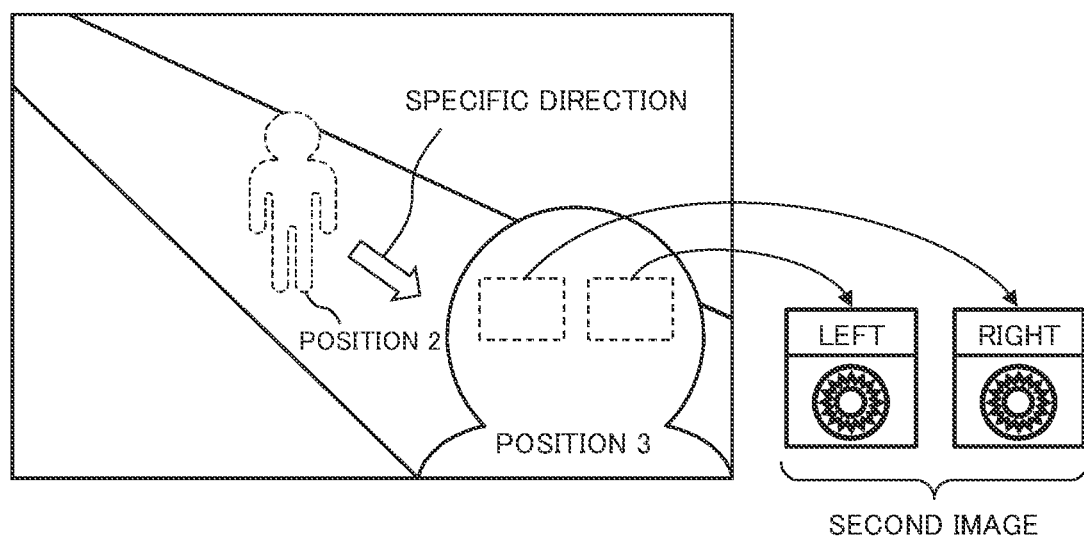
FIG. 4 is a diagram of a second image acquired from the image of the target user who moves in the specific direction.

In step S106, the detection unit 11 detects whether the target user is continuously moving in the direction from the entrance to the exit of the authentication gate (refer to FIG. 4). As a result of the detection, if the target user is moving in the direction from the entrance to the exit, the detection unit 11 acquires an image of a region of left and right eyes of the target user from the camera 10, and outputs the image to the second image input unit 13. As a result of the detection, if the target user is not moving in the direction from the entrance to the exit, the detection unit 11 instructs the first authentication unit 14 to discard the holding candidate information of the target user (step S120). The first authentication unit 14 discards the candidate information according to this instruction, and the procedure returns to step S101.

In step S107, the second image obtained by imaging an iris of at least one of the right eye and the left eye of the target user imaged by the camera 10 is input to the second image input unit 13.

In step S108, the second authentication unit 16 receives the candidate information from the first authentication unit 14, compares the characteristic information of the iris calculated from the second image with the characteristic information of one or more irises stored in the second storage unit 17 for each target user included in the candidate information, and calculates a verification score. The second authentication unit 16 authenticates the target user imaged in the first image and the second image on the basis of the calculated verification score and outputs the authentication result to the display unit 20.

In step S109, the display unit 20 displays the input authentication result. The display unit 20 displays the input authentication result.

With that, the operation of the biometric authentication device 100 is terminated.

Effects of First Example Embodiment

According to the first example embodiment, it is possible to execute highly accurate biometric authentication on an authentication target user who is moving with less hardware resources and within a predetermined time period. This is because the first authentication unit 14 narrows candidates of the target user on the basis of the image of the entire body of the target user, and the second authentication unit 16 determines whether the target user is a registered user (valid user) from among the candidates of the target user on the basis of the image of the iris of the target user. First, gait authentication or human shape authentication is executed on the target user near the entrance of the authentication gate at a remote place as the first authentication. Next, according to the result of the first authentication, iris authentication is executed on the target user who has moved near the exit of the authentication gate in the vicinity. Because candidates of the target user are narrowed by the first authentication, the number of target user candidates on which the iris authentication is executed is considerably small. As a result, an authentication result with high accuracy can be quickly obtained. Because the first authentication and the second authentication are separately executed with a time difference, two types of authentication can be executed without using a large number of hardware resources. The detection unit 11 detects only a user who moves in the predetermined direction in the authentication execution area, and excludes the user from the detection target in a case where the user stops moving in the predetermined direction. Therefore, the first authentication unit 14 and the second authentication unit 16 can execute authentication processing only on the target user. This can contribute to the quick authentication with high accuracy that does not need a large number of hardware resources.

Second Example Embodiment

As features of the iris, colors and shapes of left and right irises of the same person are different from each other. Therefore, the features of the left and the right irises are also different from each other. Therefore, even in a case of the same person, there is an eye that can be easily identified or an eye that is difficult to be identified. The eye that can be easily identified needs a short time for the authentication processing and is identified with higher accuracy. Therefore, it is possible to execute authentication with higher accuracy in a shorter time when the authentication processing is executed using the left or right eye that can be more easily identified. In the second example embodiment, a biometric authentication device or the like that executes the authentication processing while weighting the eye that can be easily identified will be described.

Biometric Authentication Device

Figure 6:
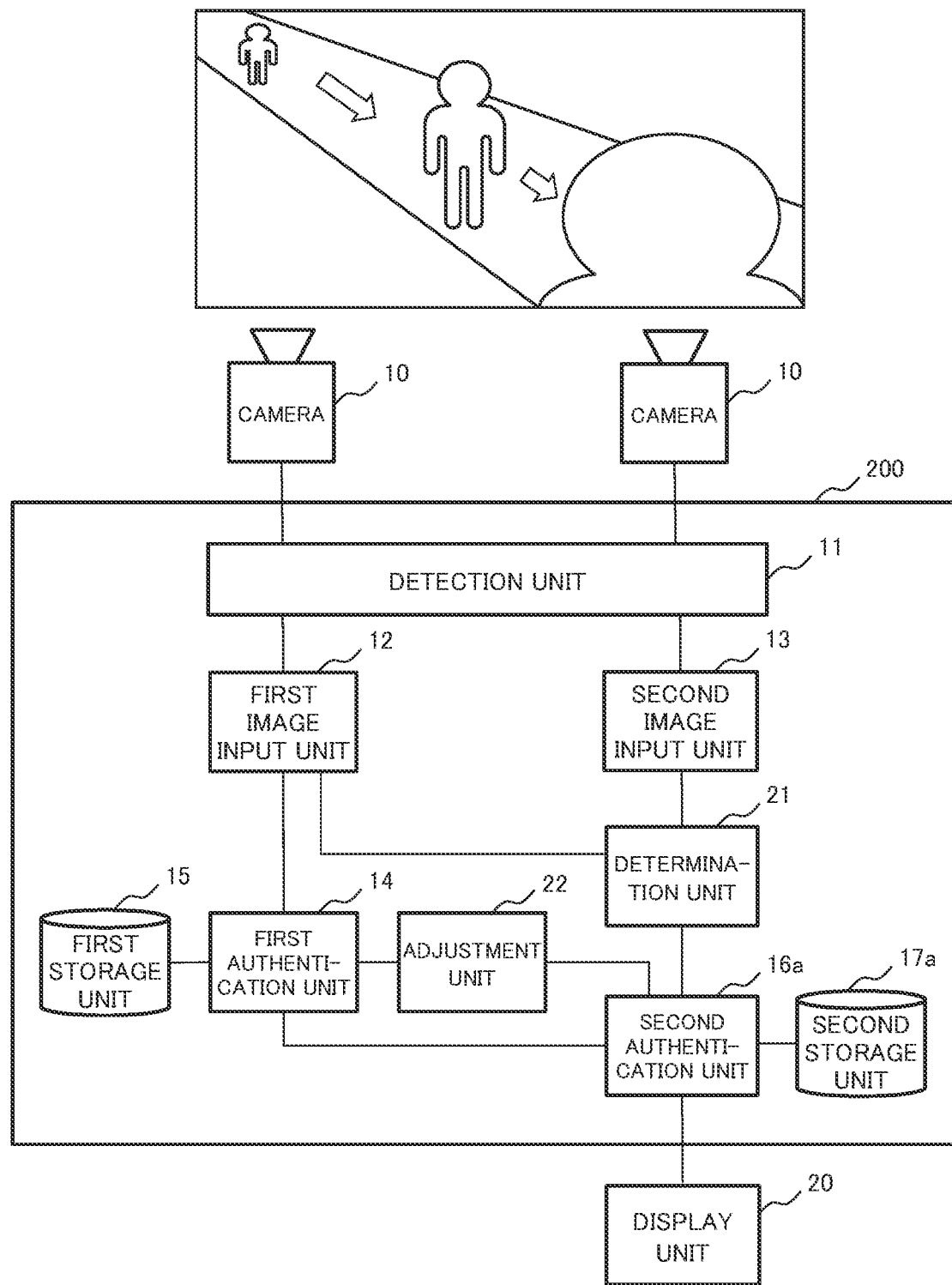
FIG. 6 is a diagram of a configuration of a biometric authentication device according to a second example embodiment of the disclosure.

As illustrated in FIG. 6, a biometric authentication device 200 includes a detection unit 11, a first image input unit 12, a second image input unit 13, a first authentication unit 14, a first storage unit 15, a second authentication unit 16a, a second storage unit 17a, a determination unit 21, and an adjustment unit 22. Note that the detection unit 11 is connected to an external camera 10. The second authentication unit 16a is connected to an external display unit 20.

The second storage unit 17a stores characteristic information and a reliability score of a right eye of each user and characteristic information and a reliability score of a left eye for each identifiable ID that is associated with a user to be authenticated (refer to FIG. 7). The reliability is a value that indicates how easy the target user and other user are identified, and the reliability score indicates the reliability as a value of zero to 100%. An example of a method for calculating the reliability score will be described. Each ID of the registered user stored in the second storage unit 17a is set to i (i={1, 2, 3, ..., N}; N, N indicates total number of registered users), characteristic information (characteristic vector) of an iris image of a right eye of each registered user is set to $X_{right}$ (i), characteristic information (characteristic vector) of an iris image of a right eye of a current target user (person to be collated) is set to $Y_{right}$, and a correlation (for example, normalized cross-correlation) between $X_{right}$ (i) and $Y_{right}$ is calculated for all the registered users i. After the calculation, a ratio (=largest correlation value/second correlation value) between the largest correlation value (that is, correlation value between identical persons (a case where target user matches registered user)) and a second correlation value (correlation value between person and registered user who is other person having highest correlation value), and the calculated value is set as a reliability $S_{right}$. Similarly, similar processing is executed on the left eye, and the calculated value is set as a reliability $S_{left}$. These reliabilities $S_{right}$ and $S_{left}$ are normalized and are converted into values of zero % to 100% in such a way as to obtain reliability scores (for example, left eye 20%, right eye 80%). Although there are various methods for normalizing the reliability, for example, when the reliability score is calculated as (%)=100×(S−1)/(M−1) (at this time, 1≤S≤M; S indicates either one of $S_{right}$ or $S_{left}$, M indicates maximum value of reliability. Maximum value is set by designer or the like in advance, and reliability in a case of M<S is set as 100). The method for calculating the reliability score is not limited to the above. As the value of the reliability score increases, the characteristic information of the target user can be more easily identified than the characteristic information of the other user (rare iris code). For example, in a case of a user ID "1" illustrated in FIG. 7, because a reliability score of the right eye is 80% and a reliability score of the left eye is 20%, an iris of the right eye of this user is characteristic, and this indicates that there are relatively less users who have similar characteristic information. On the other hand, an iris of the left eye of the user is not very characteristic, and this indicates that there are a large number of users who have similar characteristic information. In such a case, because to use the right eye is efficient for the authentication processing, even in a case where second images of both eyes can be imaged, it can be said that it is desirable to execute the authentication processing using the second image of the right eye. On the other hand, in a case where only the second image of the left eye can be imaged for some reason, even if a verification score of the authentication is low, it is possible to estimate that the low verification score is caused by the low reliability score of the left eye. In this case, the biometric authentication device 200 can request the user to image an iris image again. Specifically, the biometric authentication device 200 requests the user to move from the entrance gate to the exit gate again for authentication via the display unit 20 or the like. In a case where the eye having the higher score is hidden by hairs or the like, the second authentication unit 16a may present a document or the like, on the display unit 20, that requests the user to cooperate to clearly image the eye having the higher reliability score with the camera 10.

In addition to the operation of the second authentication unit 16 in FIG. 1, the second authentication unit 16a executes authentication using a value obtained by adding the reliability score to the verification score. The second authentication unit 16a calculates a verification score obtained by comparing characteristic information of an iris calculated from a second image associated with left/right information with one or more pieces of characteristic information stored in the second storage unit 17a related to the left/right information. Moreover, the second authentication unit 16a specifies a target user on the basis of the verification score, acquires a reliability score related to the target user from the second storage unit 17a, and calculates a score in which the reliability score is reflected on the calculated verification score. For example, if the user has the ID of "1" in FIG. 7, a reliability score of the right eye is 80%, and a reliability score of the left eye is 20%. Therefore, in a case where the verification scores of the second images of both eyes are calculated, the second authentication unit 16a weights the verification score of the right eye with the reliability score of the right eye and weights the verification score of the left eye with the reliability score of the left eye. At this time, the second authentication unit 16a may increase a priority of the eye having a higher reliability and may weight only the verification score of the right eye with the reliability score of the right eye. As a result, a score with a higher reliability can be obtained. The weighting indicates, for example, to obtain a calculation result by multiplying or adding both scores or substituting both scores into a predetermined formula. The second authentication unit 16a executes the authentication processing using the weighted score.

The determination unit 21 determines which one of images of the left eye or the right eye of the user the second image is on the basis of information including the first image and outputs left/right information indicating a determination result in association with the second image. As will be described later, the determination unit 21 outputs an image of an iris portion as illustrated in FIG. 4. In the example embodiment, for the determination regarding the left and the right eyes, as an example, one of the two following methods is used. As a first method, the determination unit 21 executes matching processing by applying a predetermined template, used to detect a positional relationship between a contour, both eyes, or the like of the face, to a face region of the user in the first image and determines which one of the left eye or the right eye of the user the second image is. To detect the positional relationship between the both eyes, the face of the user needs to face the front side of the camera 10. However, by setting the camera 10 at a position where the camera 10 can image a user who is moving toward a predetermined traveling direction, a user who faces the camera 10 is inevitably set as a determination target. As a second method, the determination unit 21 compares pixels in regions of the right eye and the left eye of the user in the first image with pixels in regions of the right eye and the left eye of the user in the second image and determines whether the second image is relevant to the left eye or the right eye of the user. In this case, the determination unit 21 extracts the pixels in the each regions of the right eye and the left eye of the user in the first image that is an image of an entire body, compares the extracted pixels with the pixels of the regions of eyes imaged in the second image, and determines which one of the left eye or the right eye the eye imaged in the second image is, according to a similarity with the compared pixel. For the comparison of the pixels, a contour tracing algorithm using a chain code, a principal component analysis method, a three-dimensional phase limited correlation method, or the like may be used. The method for determining the left and the right eyes is not limited to the above.

The first image and the second image may be imaged by the single camera 10. However, in this case, it is preferable that the camera 10 can quickly switch a magnification of a telescopic function used to image a first image and a second image of a subject.

The adjustment unit 22 adjusts an imaging time. The adjustment unit 22 performs adjustment in such a way that the second authentication unit 16 executes second authentication after first authentication by the first authentication unit 14 and the first authentication and the second authentication are completed within a time period in which the detection unit 11 can detect a target user who is moving in a predetermined direction in a video of an authentication execution area. That is, although each target user passes through from an entrance of an authentication gate to an exit in several seconds to several tens of seconds individually, if the first authentication and the second authentication are not completed within this time period, the target user cannot terminate the authentication and exit from the exit. In consideration of a moving speed of the target user, the adjustment unit 22 adjusts a timing of the first authentication by the first authentication unit 14 and a timing of the second authentication by the second authentication unit 16a and smoothly completes the authentication processing before the target user exits from the exit of the authentication gate.

Operations of the other units are similar to those of the first example embodiment.

Operation of Biometric Authentication Device

An operation of the biometric authentication device 200 according to the second example embodiment will be described with reference to the flowchart in FIG. 8. Note that it is assumed that the first storage unit 15 store in advance the characteristic information of the entire body of the plurality of users who may be an authentication target. It is assumed that the second storage unit 17a stores characteristic information of irises of the right eye and the left eye of the plurality of users who may be an authentication target and a reliability score (refer to FIG. 7) in advance.

Figure 5:
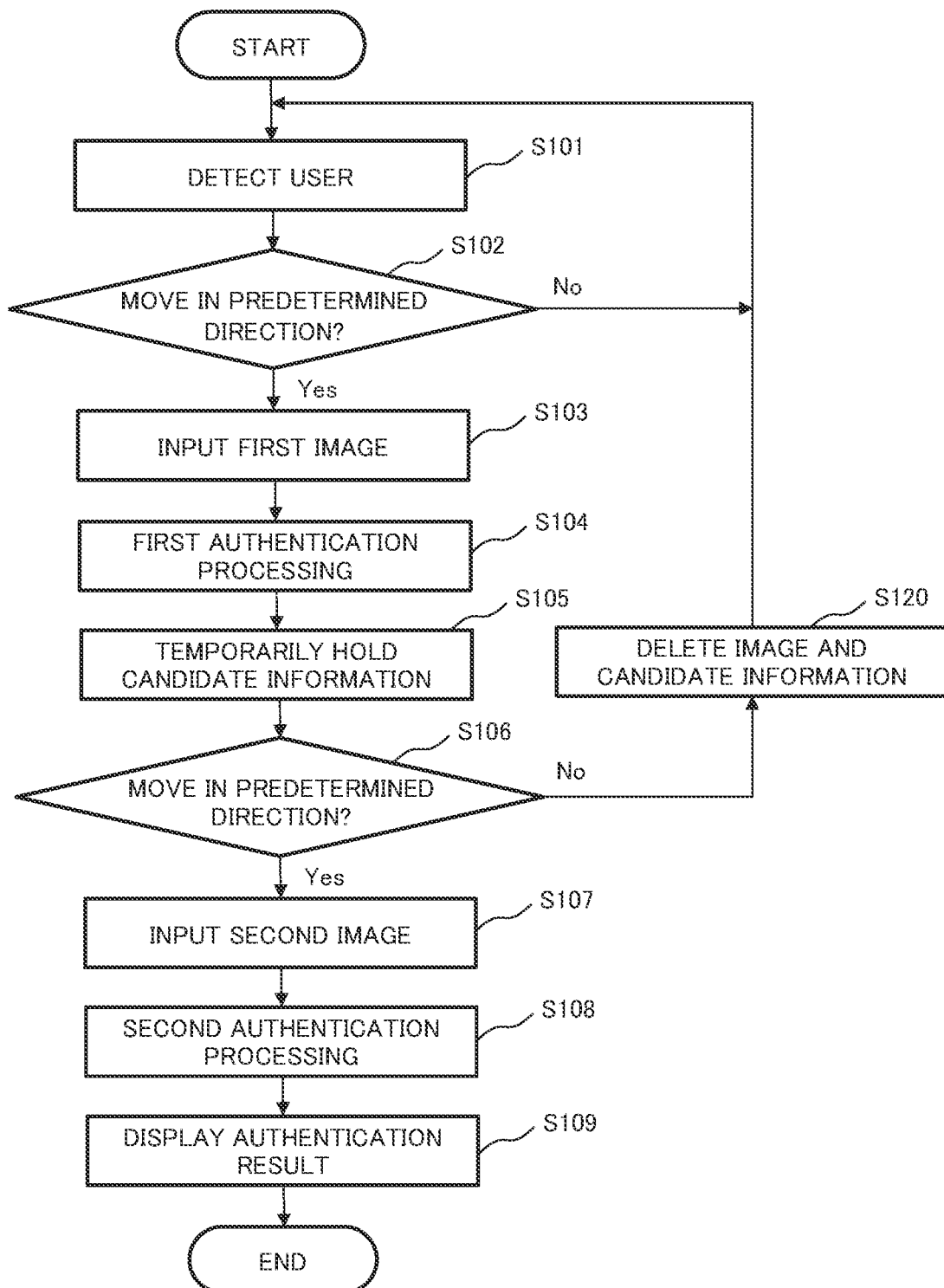
FIG. 5 is a flowchart illustrating an operation example of the biometric authentication device according to the first example embodiment of the disclosure.

Steps S201 to S207 and S220 are similar to steps S101 to S107 and S120 in FIG. 5.

In step S208, the determination unit 21 determines which one of the left eye or the right eye of the target user the second image is on the basis of the information including the first image and outputs a determination result to the second authentication unit 16a in association with the second image as the left/right information.

In step S209, the second authentication unit 16a receives candidate information of the target user from the first authentication unit 14. Moreover, the second authentication unit 16a receives the second image associated with the left/right information from the determination unit 21. The second authentication unit 16a compares characteristic information of the iris calculated from the received second image with characteristic information of the target user included in the candidate information stored in the second storage unit 17 related to the left/right information and calculates a verification score. The second authentication unit 16a specifies a target user on the basis of the calculated verification score, acquires a reliability score related to the target user from the second storage unit 17a, and weights the calculated verification score with the reliability score (hereinafter, described as weighted verification score). At this time, the second authentication unit 16a may prioritize an eye having a higher reliability and weight a verification score of the eye having the higher priority with a reliability score of the eye. The second authentication unit 16a authenticates the target user imaged in the first image and the second image on the basis of the weighted score. Specifically, the second authentication unit 16a authenticates that the user imaged in the first image and the second image is a registered user (valid user) if the weighted verification score is equal to or more than a predetermined threshold and authenticates that the user imaged in the first image and the second image is not the registered user if the weighted verification score is equal to or less than a predetermined threshold.

In step S210, the second authentication unit 16a outputs an authentication result to the external display unit 20. The display unit 20 displays the input authentication result.

With that, the operation of the biometric authentication device 200 is terminated.

Effect of Second Example Embodiment

According to the second example embodiment, it is possible to execute the authentication processing with higher accuracy, in addition to the effect of the first example embodiment. This is because the second authentication unit 16a specifies the target user from the second storage unit 17a on the basis of the calculated verification score, acquires the reliability score related to the target user from the second storage unit 17a, and weights the calculated verification score with the reliability score. Moreover, this is because the second authentication unit 16a prioritizes the eye having the higher reliability and weights the verification score of the eye having the higher priority with the reliability score of the eye.

Third Example Embodiment

In the first and the second example embodiments, only the entire body authentication (human shape authentication or gait authentication) and the iris authentication are executed. However, multi-modal authentication combined with third authentication different from the first authentication and the second authentication may be executed. For example, in the first and the second example embodiments, because the entire body image and the left and the right eye images of the moving user are used, it is preferable to execute face authentication between the first authentication (entire body) and the second authentication (eye) from the viewpoint of a timing of authentication target detection. In the third example embodiment, a biometric authentication device or the like in which three types of biometric authentication are combined will be described.

Biometric Authentication Device

Figure 9:
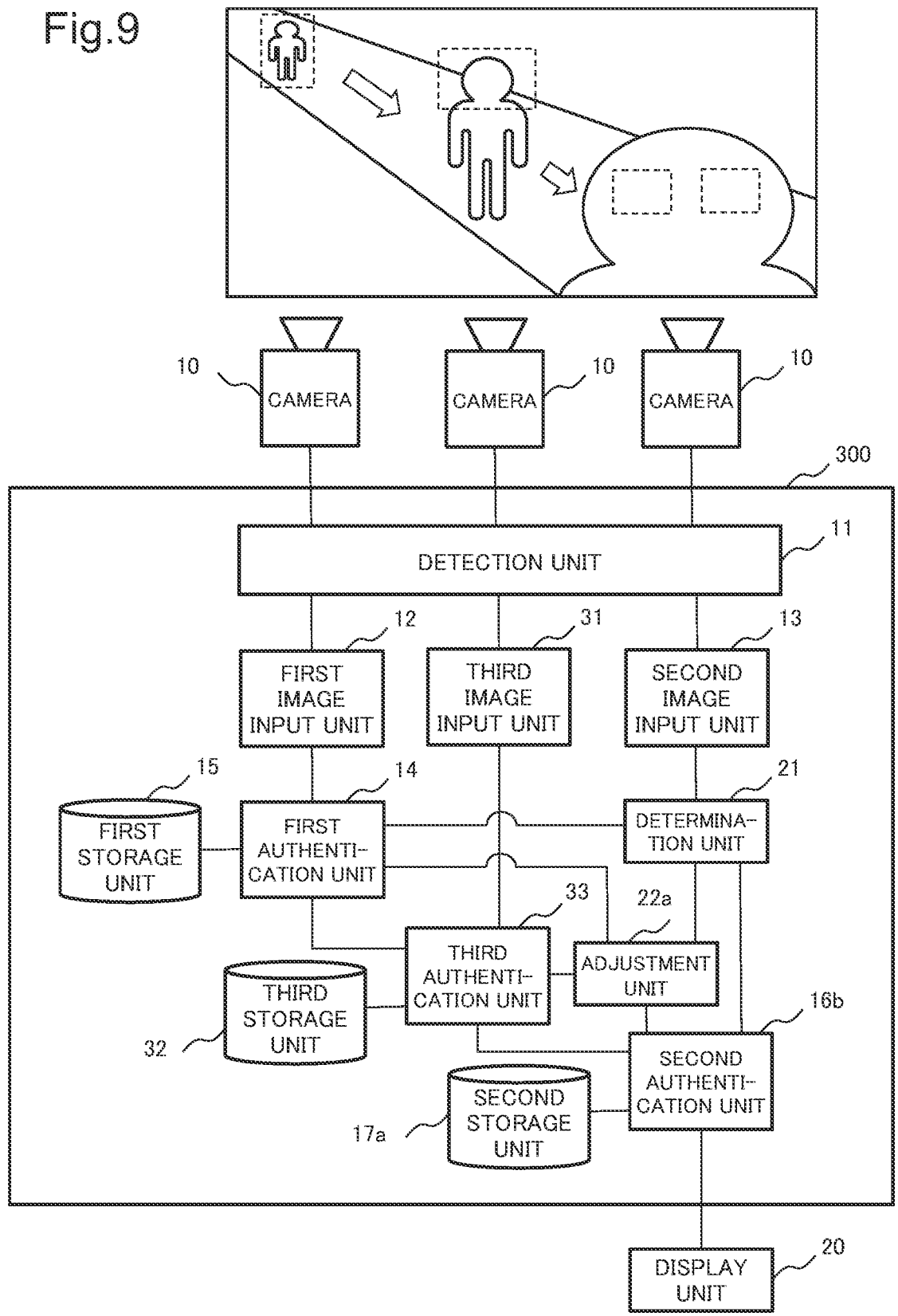
FIG. 9 is a diagram illustrating an exemplary configuration of a biometric authentication device according to a third example embodiment of the disclosure.

As illustrated in FIG. 9, a biometric authentication device 300 includes a detection unit 11, a first image input unit 12, a second image input unit 13, a first authentication unit 14, a first storage unit 15, a second authentication unit 16b, a second storage unit 17a, a determination unit 21, an adjustment unit 22a, a third image input unit 31, a third storage unit 32, and a third authentication unit 33. The detection unit 11 is connected to an external camera 10. The second authentication unit 16b is connected to an external display unit 20.

The third image input unit 31 inputs a third image in which a face region of a target user who is moving in a predetermined direction and is detected by the detection unit 11 is imaged between an input of an image by the first image input unit 12 and an input of an image by the second image input unit 13.

The third storage unit 32 stores characteristic information of faces of one or more users to be authenticated. The characteristic information of the face is, for example, feature points indicating characteristic shapes, a positional relationship, or the like of eyes, a nose, an a mouth end in the face extracted as a face feature amount.

The third authentication unit 33 compares characteristic information of the face calculated from the third image with the characteristic information of one or more faces stored in the third storage unit for each target user included in candidate information output in first authentication, calculates a second verification score and extracts candidate information of one or more target users from the third storage unit on the basis of the calculated second verification score. The third authentication unit 33 outputs the extracted candidate information to the second authentication unit 16b.

Although the second authentication unit 16b has a function similar to the second authentication unit 16 (refer to FIG. 1) and the second authentication unit 16a (refer to FIG. 6) described above, the second authentication unit 16b executes iris authentication of the target user on the basis of the candidate information input from the third authentication unit 33.

The adjustment unit 22a adjusts an authentication timing in such a way that the third authentication is executed after the first authentication, the second authentication is executed after the third authentication, and the first authentication, the third authentication, and the second authentication are completed within a time period in which a target user who is moving in a predetermined direction in a video of an authentication execution area can be detected.

Operations of other units are similar to those in the first and second example embodiments.

Operation of Biometric Authentication Device

Figure 10:
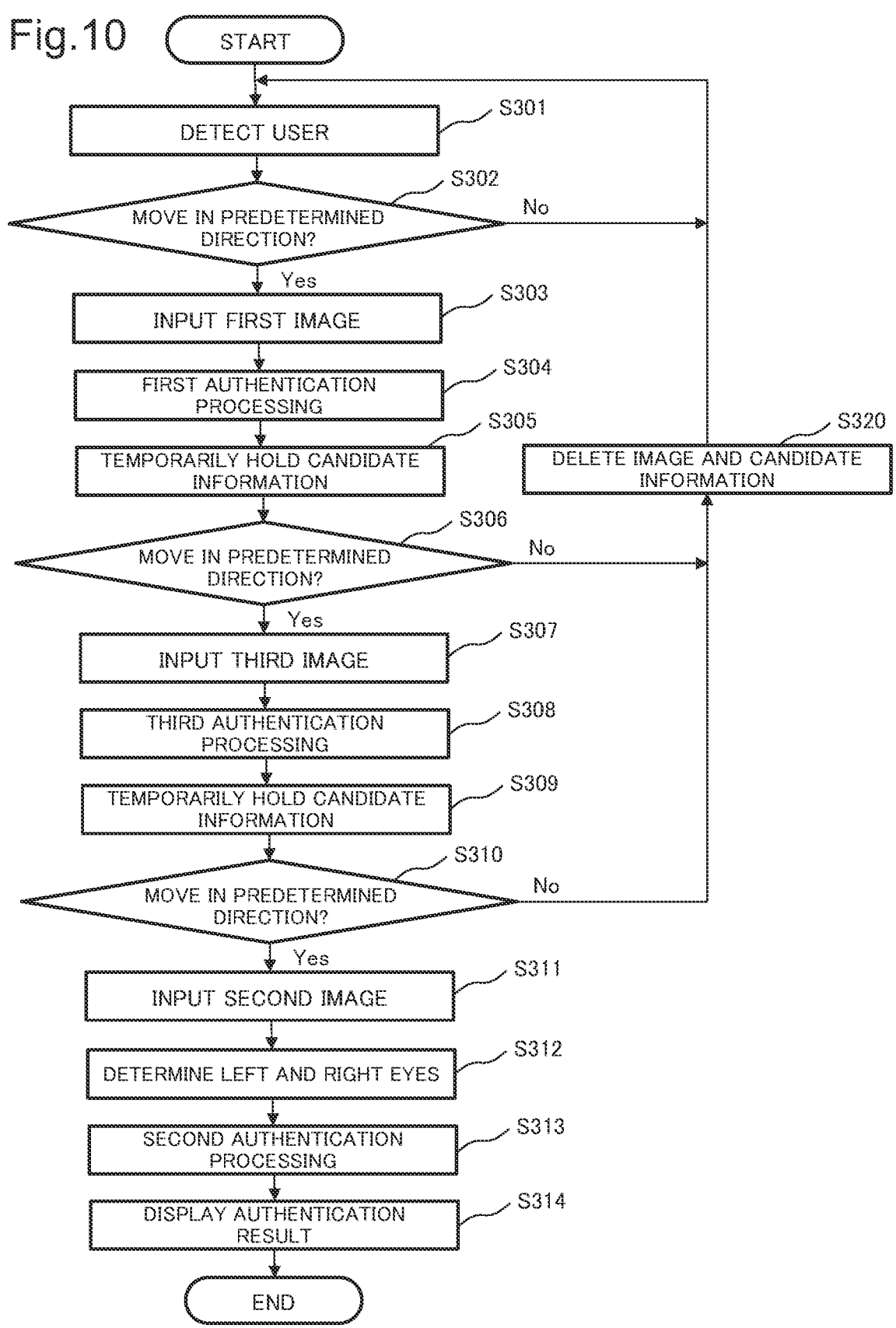
FIG. 10 is a flowchart illustrating an operation example of the biometric authentication device according to the third example embodiment of the disclosure.

An operation of the biometric authentication device 300 according to the third example embodiment will be described with reference to the flowchart in FIG. 10. Note that it is assumed that the first storage unit 15 store in advance the characteristic information of the entire body of the plurality of users who may be an authentication target. It is assumed that the second storage unit 17a stores in advance characteristic information of irises of the right eye and the left eye of the plurality of users who may be an authentication target. The characteristic information of the iris may store information to which a reliability score is added (refer to FIG. 7). It is assumed that the third storage unit 32 store characteristic information of the faces of the plurality of users to be authenticated in advance.

Figure 8:
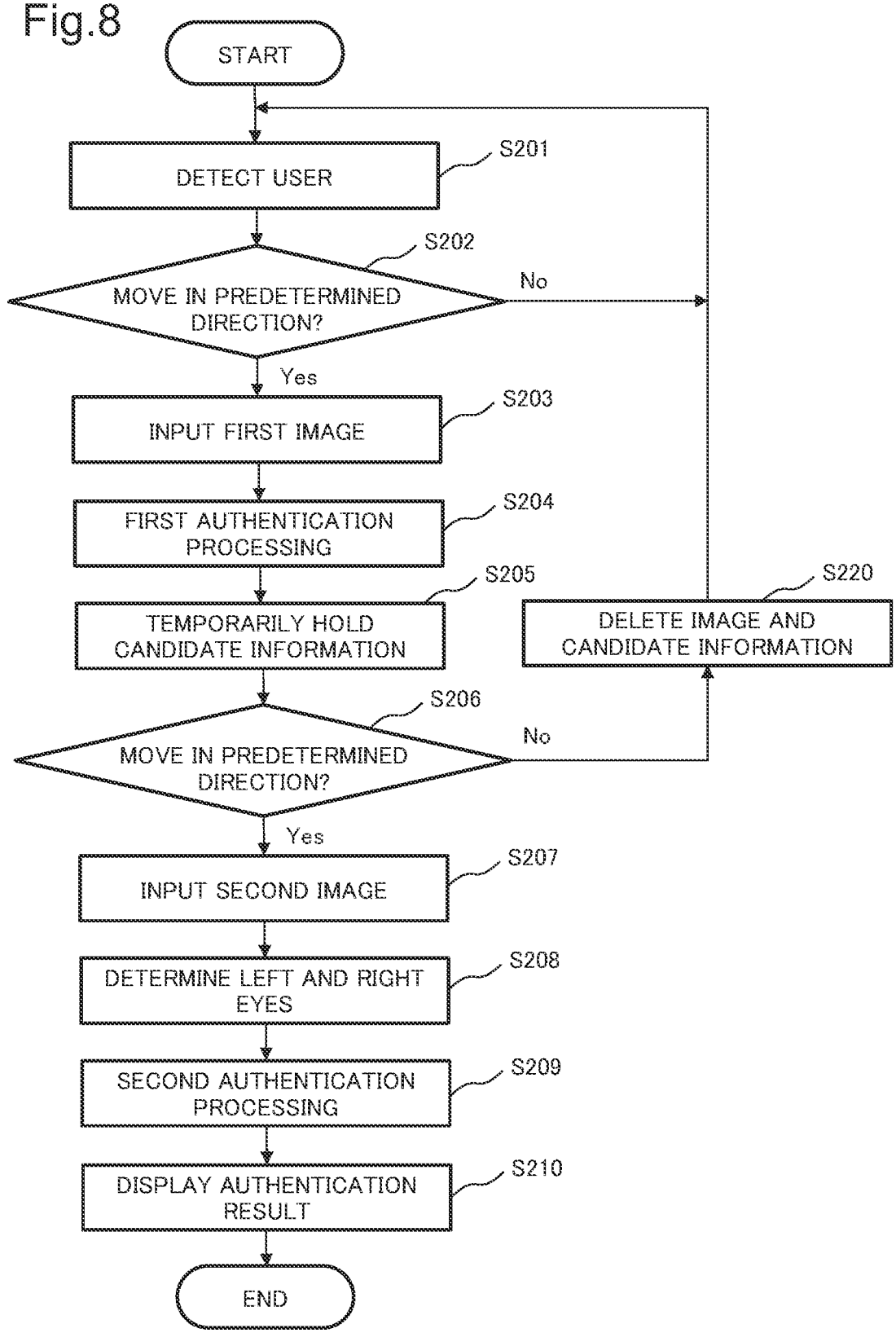
FIG. 8 is a flowchart illustrating an operation example of the biometric authentication device according to the second example embodiment of the disclosure.

Steps S301 to S305 and S320 are similar to steps S201 to S205 and S220 in FIG. 8.

In step S306, the detection unit 11 detects whether a user is moving in a direction from an entrance to an exit of an authentication gate. As a result of the detection, if the user is moving in the direction from the entrance to the exit, the detection unit 11 acquires an image of a face of the target user from the camera 10 and outputs the image to the third image input unit 31. As a result of the detection, if the user is not moving in the direction from the entrance to the exit, the procedure proceeds to step S320, and returns to step S301 after the image and the candidate information that are temporarily held by the first authentication unit 14 are deleted.

In step S307, the third image input unit 31 inputs a third image in which the face of the target user is imaged. At this time, the third image input unit 31 may select a face region from the image of the target user and input the selected region as the third image.

In step S308, the third authentication unit 33 calculates characteristic information from the image of the face region of the target user imaged in the third image, compares the calculated characteristic information with the characteristic information of the face stored in the third storage unit 32, and extracts candidate information of one or more target users from the third storage unit 32 on the basis of a comparison result.

In step S309, the third authentication unit 33 temporarily holds the extracted candidate information of the target user.

Steps S310 to S314 are similar to steps S206 to S210 in FIG. 8.

With that, the operation of the biometric authentication device 300 is terminated.

Effect of Third Example Embodiment

According to the third example embodiment, it is possible to provide the biometric authentication device 300 that has higher authentication accuracy than the biometric authentication devices described in the first and second example embodiments, in addition to the effects of the first and second example embodiments. This is because the face authentication is combined as the third authentication between the first authentication (entire body) and the second authentication (eye). Moreover, this is because, the gait authentication or the like (entire body), the face authentication (face), the iris authentication (left and right eyes), and after arrangements of authentication position that most easily images the target user according to the movement of the target user are combined from the entrance to the exit of the authentication execution area, the adjustment unit 22a adjusts the authentication timing in such a way that the first authentication to the third authentication are completed, in order of the first authentication, the third authentication, and the second authentication, within a time period in which the target user who is moving in the predetermined direction in the video of the authentication execution area can be detected.

The example embodiments may be used in combination.

Information Processing Device

Figure 11:
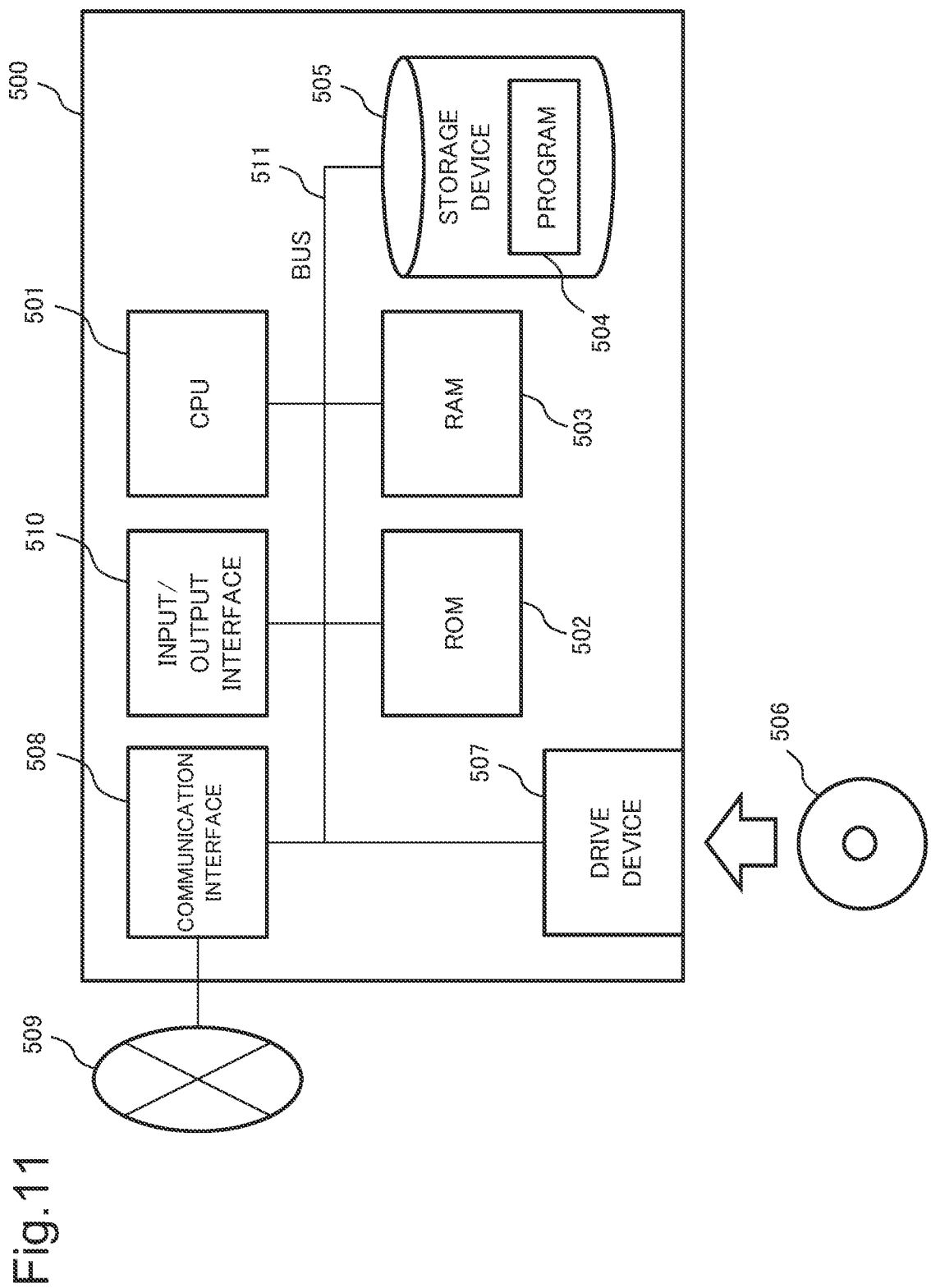
FIG. 11 is a diagram of a configuration of an information processing device that can be used in the first to the third example embodiments.

In each example embodiment described above, some or all of the components of the biometric authentication devices illustrated in FIGS. 1, 6, 9, or the like can be achieved, for example, by using any combination of an information processing device 500 and a program as illustrated in FIG. 11. The information processing device 500 includes, for example, the following configurations.

Central Processing Unit (CPU) 501
Read Only Memory (ROM) 502
Random Access Memory (RAM) 503

Storage device 505 that stores program 504 and other pieces of data
Drive device 507 that reads/writes from/to recording medium 506
Communication interface 508 that connects to communication network 509
Input/output interface 510 that inputs/outputs data
Bus 511 that connects components Each component of the biometric authentication device in each example embodiment of the application is achieved by the CPU 501 acquiring and executing the program 504 that enables the functions of these constituent elements. The program 504 that achieves the function of each component of the biometric authentication device is stored, for example, in the storage device 505 and the RAM 503 in advance and is read by the CPU 501 as needed. The program 504 may be supplied to the CPU 501 via the communication network 509, or the program 504 may be stored in the recording medium 506 in advance and the drive device 507 may read the program and supply the read program to the CPU 501.

There are various modifications of the method for achieving each device. For example, the biometric authentication device may be achieved by any combination of an individual information processing device and a program for each component. The plurality of components included in the biometric authentication device may be achieved by any combination of a single information processing device 500 and a program.

Some or all of the components of the biometric authentication device are achieved by other general or dedicated circuits, processors, or the like, and a combination thereof. These may be configured by a single chip or a plurality of chips connected via a bus.

Some or all of the components of the biometric authentication device may be achieved by a combination of the circuit or the like and the program described above.

In a case where some or all of the components of the biometric authentication device are achieved by a plurality of information processing devices, circuits, or the like, the plurality of information processing devices, circuits, or the like may be centrally or dispersedly arranged. For example, the information processing device, the circuit, or the like may be achieved as a form in which each one is connected via a communication network, such as a client server system, a cloud computing system, or the like.

The whole or part of the example embodiments disclosed above can be described as, but not limited to, the following supplementary notes.

Supplementary Note 1

An authentication device comprising:
detection means for detecting an authentication target who is moving in a predetermined direction in a video of a predetermined area;
first image input means for inputting a first image in which an entire body of the detected target is imaged;
first storage means for storing characteristic information of entire bodies of one or more targets to be authenticated;
first authentication means for calculating characteristic information from an image of the entire body of the target imaged in the first image, comparing the calculated characteristic information with the characteristic information of the entire body stored in the first storage means, and extracting candidate information of the one or more targets from the first storage means based on a comparison result;

second image input means for inputting a second image in which an iris of at least one of a right eye and a left eye of the target who is detected by the detection means and is moving in the predetermined direction is imaged;

second storage means for storing characteristic information of irises of the right eyes and the left eyes of the one or more targets to be authenticated; and second authentication means for comparing characteristic information of the iris calculated from the second image with the characteristic information of one or more irises stored in the second storage means, calculating a verification score for each target included in the candidate information, authenticating the target imaged in the second image based on the calculated verification score, and outputting an authentication result.

Supplementary Note 2

The authentication device according to supplementary note 1, in which when the detection means detects a movement of the target in a direction other than the predetermined direction, the first image input means and the second image input means stop input of an image of the target.

Supplementary Note 3

The authentication device according to supplementary note 1 or 2, further comprising:

determination means for determining whether the second image is of the left eye or the right eye of the target based on information including the first image and outputting a determination result in association with the second image as left/right information, in which the second authentication means compares characteristic information of an iris calculated from the second image associated with the left/right information with one or more pieces of characteristic information stored in the second storage means related to the left/right information and calculates the verification score.

Supplementary Note 4

The authentication device according to supplementary note 1, in which the second storage means stores the characteristic information of the irises of the right eyes and the left eyes of the one or more targets to be authenticated and reliability scores of the right eyes and the left eyes of the one or more targets to be authenticated, and the second authentication means specifies the target based on the verification score, acquires the reliability score related to the target from the second storage means, and calculates a weighted verification score obtained by weighting the reliability score to the verification score.

Supplementary Note 5

The authentication device according to any one of supplementary notes 1, 3, and 4, in which the second authentication means prioritizes an eye having a higher value indicating the reliability score and calculates the weighted verification score.

Supplementary Note 6

The authentication device according to supplementary note 3, in which the determination means applies a predetermined template to a face region of the target in the first image and determines whether the two images are relevant to the left eye or the right eye of the target.

Supplementary Note 7

The authentication device according to supplementary note 1, further comprising:

adjustment means for performing adjustment in such a way that the second authentication means executes second authentication after first authentication by the first authentication means and the first authentication and the second authentication are completed within a time period in which the detection means is able to detect the target who is moving in the predetermined direction in the video of the predetermined area.

Supplementary Note 8

The authentication device according to supplementary note 1, further comprising:

third image input means for inputting a third image in which a face of the target who is moving in the predetermined direction and is detected by the detection means is imaged between input of an image by the first image input means and input of an image by the second image input means;

third storage means for storing characteristic information of faces of the one or more targets to be authenticated; and third authentication means for comparing characteristic information of the face calculated from the third image with the characteristic information of the one or more faces stored in the third storage means for each target included in the candidate information output by the first authentication means and extracting candidate information of the one or more targets from the third storage means based on a comparison result.

Supplementary Note 9

The authentication device according to supplementary note 7, in which the adjustment means performs adjustment in such a way that the third authentication means executes third authentication after the first authentication by the first authentication means, the second authentication means executes the second authentication after the third authentication, and the first authentication, the third authentication, and the second authentication are completed within a time period in which the detection means is able to detect the target who is moving in the predetermined direction in the video of the predetermined area.

Supplementary Note 10

An authentication method comprising:

detecting an authentication target who is moving in a predetermined direction in a video of a predetermined area;

inputting a first image in which an entire body of the detected target is imaged;

calculating characteristic information from an image of the entire body of the target imaged in the first image, comparing the calculated characteristic information with characteristic information of the entire body stored in first storage means that stores characteristic information of entire bodies of one or more targets to be authenticated to execute first authentication, and extracting candidate information of the one or more targets from the first storage means based on a result of the first authentication;

inputting a second image in which an iris of at least one of a right eye and a left eye of the target who is detected and is moving in the predetermined direction is imaged; and comparing characteristic information of one or more irises stored in second storage means that stores characteristic information of irises of the right eyes and the left eyes of the one or more targets to be authenticated with characteristic information of an iris calculated from the second image for each target included in the candidate information, calculating a verification score, executing second authentication on the target imaged in the second image based on the calculated verification score, and outputting an authentication result.

Supplementary Note 11

The authentication method according to supplementary note 10, in which in the detection, when a movement of the target in a direction other than the predetermined direction is detected, inputs of a first image and a second image of the target are stopped.

Supplementary Note 12

The authentication method according to supplementary note 10 or 11, further comprising:

determining whether the second image is of the left eye or the right eye of the based on information including the first image and outputting a determination result in association with the second image as left/right information, in which in the second authentication, characteristic information of an iris calculated from the second image associated with the left/right information is compared with one or more pieces of characteristic information stored in the second storage means related to the left/right information, and the verification score is calculated.

Supplementary Note 13

The authentication method according to supplementary note 10, in which the second storage means stores the characteristic information of the irises of the right eyes and the left eyes of the one or more targets to be authenticated and reliability scores of the right eyes and the left eyes of the one or more targets to be authenticated, and in the second authentication, the target is specified based on the verification score, the reliability score related to the target is acquired from the second storage means, and a weighted verification score obtained by weighting the reliability score to the verification score is calculated.

Supplementary Note 14

The authentication method according to any one of supplementary notes 10, 12, and 13, in which in the second authentication, an eye having a higher value indicating the reliability score is prioritized, and the weighted verification score is calculated.

Supplementary Note 15

The authentication method according to supplementary note 12, in which in the determination, a predetermined template is applied to a face region of the target in the first image, and it is determined whether the two images are relevant to the left eye or the right eye of the target.

Supplementary Note 16

The authentication method according to supplementary note 10, further comprising:

performing adjustment in such a way that the second authentication is executed after the first authentication, and the first authentication and the second authentication are completed within a time period in which it is possible to perform the detection of the target who is moving in the predetermined direction in the video of the predetermined area.

Supplementary Note 17

The authentication method according to supplementary note 10, further comprising:

inputting a third image in which a face of the detected target who is moving in the predetermined direction is imaged between input of the first image and input of the second image; and comparing characteristic information of the face calculated from the third image with the characteristic information of the one or more faces stored in third storage means that stores characteristic information of faces of the one or more targets to be authenticated for each target included in the candidate information output in the first authentication, calculating a second verification score, and extracting candidate information of the one or more targets from the third storage means based on the calculated second verification score.

Supplementary Note 18

The authentication method according to supplementary note 16, in which in the adjustment, adjustment is performed in such a way that the third authentication is executed after the first authentication, the second authentication is executed after the third authentication, and the first authentication, the third authentication, and the second authentication are completed within a time period in which it is possible to perform the detection of the target who is moving in the predetermined direction in the video of the predetermined area.

Supplementary Note 19

A storage medium that stores an authentication program for causing a computer to achieve processing comprising:

detecting an authentication target who is moving in a predetermined direction in a video of a predetermined area;

inputting a first image in which an entire body of the detected target is imaged;

calculating characteristic information from an image of the entire body of the target imaged in the first image, comparing the calculated characteristic information with characteristic information of the entire body stored in first storage means that stores characteristic information of entire bodies of one or more targets to be authenticated to execute first authentication, and extracting candidate information of the one or more targets from the first storage means based on a result of the first authentication;

inputting a second image in which an iris of at least one of a right eye and a left eye of the target who is detected and is moving in the predetermined direction is imaged; and comparing characteristic information of one or more irises stored in second storage means that stores the characteristic information of the irises of the right eyes and the left eyes of the one or more targets to be authenticated with characteristic information of an iris calculated from the second image for each target included in the candidate information, calculating a verification score, executing second authentication on the target imaged in the second image based on the calculated verification score, and outputting an authentication result.

Supplementary Note 20

The storage medium according to supplementary note 19, in which in the detection, when a movement of the target in a direction other than the predetermined direction is detected, inputs of a first image and a second image of the target are stopped.

Supplementary Note 21

The storage medium according to supplementary note 19 or 20, further comprising:

determining whether the second image is of the left eye or the right eye of the target based on information including the first image and outputting a determination result in association with the second image as left/right information, in which in the second authentication, characteristic information of an iris calculated from the second image associated with the left/right information is compared with one or more pieces of characteristic information stored in the second storage means related to the left/right information, and the verification score is calculated.

Supplementary Note 22

The storage medium according to supplementary note 19, in which the second storage means stores the characteristic information of the irises of the right eyes and the left eyes of the one or more targets to be authenticated and reliability scores of the right eyes and the left eyes of the one or more targets to be authenticated, and in the second authentication, the target is specified based on the verification score, the reliability score related to the target is acquired from the second storage means, and a weighted verification score obtained by weighting the reliability score to the verification score is calculated.

Supplementary Note 23

The storage medium according to any one of supplementary notes 19, 21, and 22, in which in the second authentication, an eye having a higher value indicating the reliability score is prioritized, and the weighted verification score is calculated.

Supplementary Note 24

The storage medium according to supplementary note 21, in which in the determination, a predetermined template is applied to a face region of the target in the first image, and it is determined whether the two images are relevant to the left eye or the right eye of the target.

Supplementary Note 25

The storage medium according to supplementary note 19, further comprising:

performing adjustment in such a way that the second authentication is executed after the first authentication, and the first authentication and the second authentication are completed within a time period in which it is possible to perform the detection of the target who is moving in the predetermined direction in the video of the predetermined area.

Supplementary Note 26

The storage medium according to supplementary note 19, further comprising:

inputting a third image in which a face of the detected target who is moving in the predetermined direction is imaged between input of the first image and input of the second image; and comparing characteristic information of the face calculated from the third image with characteristic information of one or more faces stored in third storage means that stores characteristic information of faces of the one or more targets to be authenticated for each target included in the candidate information output in the first authentication, calculating a second verification score, and extracting candidate information of the one or more targets from the third storage means based on the calculated second verification score.

Supplementary Note 27

The storage medium according to supplementary note 25, in which the adjustment is performed in such a way that the third authentication is executed after the first authentication, the second authentication is executed after the third authentication, and the first authentication, the third authentication, and the second authentication are completed within a time period in which it is possible to perform the detection of the target who is moving in the predetermined direction in the video of the predetermined area.

While the application has been particularly shown and described with reference to exemplary embodiments thereof, the application is not limited to these embodiments. It will be understood by those of ordinary skill in the art that various changes in form and details may be made therein without departing from the spirit and scope of the example embodiments as defined by the claims.

REFERENCE SIGNS LIST

10 camera
11 detection unit
12 first image input unit
13 second image input unit
14 first authentication unit
15 first storage unit
16 second authentication unit
16a second authentication unit
16b second authentication unit
17 second storage unit 17a second storage unit
20 display unit
21 determination unit
22 adjustment unit
22a adjustment unit
31 third image input unit
32 third storage unit
33 third authentication unit
100 biometric authentication device
200 biometric authentication device
300 biometric authentication device
500 information processing device
501 CPU
503 RAM
504 program
505 storage device
506 recording medium
507 drive device
508 communication interface
509 communication network
510 input/output interface
511 bus
507 drive device
508 communication interface
509 communication network
510 input/output interface
511 bus

The invention claimed is:

1. An authentication device comprising:
a memory configured to store instructions; and
at least one processor configured to execute the instructions to:
   extract first biological information of an authentication target from a first image, the authentication target moving in a predetermined direction in a video of a predetermined area;
   extract, as candidate information of the authentication target and from a storage storing a plurality of sets of registrant information about a plurality of registrants, one or more sets of registrant information from the storage by performing a first authentication using the first biological information, wherein each of the plurality of sets of registrant information stored in the storage comprises reliability scores of eyes of a respective registrant, the reliability scores indicating ease of identification between the eyes of the respective registrant and corresponding eyes of others;
   temporarily store the extracted candidate information;
   extract second biological information of the authentication target from a second image captured after the first image, the second biological information having a different type than the first biological information;
   perform iris authentication, as a second authentication having higher accuracy than the first authentication, by:
      calculating authentication target characteristic information from irises of eyes of the authentication target in the second image;
      calculating a plurality of verification scores of the authentication target, each verification score calculated by comparing the authentication target characteristic information with characteristic information of irises of the eyes of a corresponding one of the registrants referenced within the extracted candidate information;
      calculating a plurality of weighted verification scores, each weighted verification score calculated by weighting a corresponding verification score using the reliability scores of the eyes of the corresponding one of the registrants referenced within the extracted candidate information;
   authenticating the authentication target using the plurality of calculated verification scores; and
   outputting a result of authenticating the authentication target; and
   discard the temporarily stored candidate information when the authentication target does not move in the predetermined direction between a time when the first image was captured and a time when the second image was captured.

2. The authentication device according to claim 1, wherein for each of the registrants referenced within the candidate information, the characteristic information of left eye or the right eye having the higher reliability score is compared with the authentication target characteristic information of the iris a corresponding eye of the authentication target.

3. The authentication device according to claim 1, wherein the first image includes a whole body of the authentication target, and
wherein, as the first biological information, information on a human shape or a gait is extracted from the first image.

4. An authentication method comprising:
by at least one processor,
   extracting first biological information of an authentication target from a first image, the authentication target moving in a predetermined direction in a video of a predetermined area;
   extracting, as candidate information of the authentication target and from a storage storing a plurality of sets of registrant information about a plurality of registrants, one or more sets of registrant information from the storage by performing a first authentication using the first biological information, wherein each of the plurality of sets of registrant information stored in the storage comprises reliability scores of eyes of a respective registrant, the reliability scores indicating ease of identification between the eyes of the respective registrant and corresponding eyes of others;
   temporarily storing the extracted candidate information;
   extracting second biological information of the authentication target from a second image captured after the first image, the second biological information having a different type than the first biological information;
   performing iris authentication, as a second authentication having higher accuracy than the first authentication, by:
      calculating authentication target characteristic information from irises of eyes of the authentication target in the second image;
      calculating a plurality of verification scores of the authentication target, each verification score calculated by comparing the authentication target characteristic information with characteristic information of irises of the eyes of a corresponding one of the registrants referenced within the extracted candidate information;
      calculating a plurality of weighted verification scores, each weighted verification score calculated by weighting a corresponding verification score using the reliability scores of the eyes of the corresponding one of the registrants referenced within the extracted candidate information;

authenticating the authentication target using the plurality of calculated verification scores; and outputting a result of authenticating the authentication target; and discarding the temporarily stored candidate information when the authentication target does not move in the predetermined direction between a time when the first image was captured and a time when the second image was captured.

5. The authentication method according to claim 4, wherein for each of the registrants referenced within the candidate information, the characteristic information of left eye or the right eye having the higher reliability score is compared with the authentication target characteristic information of the iris a corresponding eye of the authentication target.

6. The authentication device according to claim 4, wherein the first image includes a whole body of the authentication target, and wherein, as the first biological information, information on a human shape or a gait is extracted from the first image.

7. A non-transitory storage medium storing a computer program executable by a computer to perform:

extracting first biological information of an authentication target from a first image, the authentication target moving in a predetermined direction in a video of a predetermined area;

extracting, as candidate information of the authentication target and from a storage storing a plurality of sets of registrant information about a plurality of registrants, one or more sets of registrant information from the storage by performing a first authentication using the first biological information, wherein each of the plurality of sets of registrant information stored in the storage comprises reliability scores of eyes of a respective registrant, the reliability scores indicating ease of identification between the eyes of the respective registrant and corresponding eyes of others;

temporarily storing the extracted candidate information;

extracting second biological information of the authentication target from a second image captured after the first image, the second biological information being having a different type than the first biological information;

performing iris authentication, as a second authentication having higher accuracy than the first authentication, by:

calculating authentication target characteristic information from irises of eyes of the authentication target in the second image;

calculating a plurality of verification scores of the authentication target, each verification score calculated by comparing the authentication target characteristic information with characteristic information of irises of the eyes of a corresponding one of the registrants referenced within the extracted candidate information;

calculating a plurality of weighted verification scores, each weighted verification score calculated by weighting a corresponding verification score using the reliability scores of the eyes of the corresponding one of the registrants referenced within the extracted candidate information;

authenticating the authentication target using the plurality of calculated verification scores; and outputting a result of authenticating the authentication target; and discarding the temporarily stored candidate information when the authentication target does not move in the predetermined direction between a time when the first image was captured and a time when the second image was captured.

8. The non-transitory storage medium according to claim 7, wherein for each of the registrants referenced within the candidate information, the characteristic information of left eye or the right eye having the higher reliability score is compared with the authentication target characteristic information of the iris a corresponding eye of the authentication target.

9. The authentication device according to claim 7, wherein the first image includes a whole body of the authentication target, and wherein, as the first biological information, information on a human shape or a gait is extracted from the first image.

* * * * *